(12) United States Patent
Hauser et al.

(10) Patent No.: US 10,692,219 B2
(45) Date of Patent: Jun. 23, 2020

(54) METHOD AND SYSTEM FOR RECONSTRUCTING 3-DIMENSIONAL IMAGES FROM SPATIALLY AND TEMPORALLY OVERLAPPING X-RAYS

(71) Applicant: ADAPTIX LTD., Oxfordshire (GB)

(72) Inventors: Raphael Hauser, Oxford (GB); Maria Klodt, Oxford (GB); Gil Travish, Oxford (GB); Paul Betteridge, Witney (GB)

(73) Assignee: Adaptix Ltd., Harwell (GB)

( * ) Notice: Subject to any disclaimer, the term of this patent is extended or adjusted under 35 U.S.C. 154(b) by 0 days.

(21) Appl. No.: 16/271,719

(22) Filed: Feb. 8, 2019

(65) Prior Publication Data
US 2019/0265174 A1 Aug. 29, 2019

Related U.S. Application Data

(63) Continuation of application No. PCT/GB2017/000521, filed on Jul. 19, 2017, which is
(Continued)

(51) Int. Cl.
*G06T 7/174* (2017.01)
*G06T 7/00* (2017.01)
(Continued)

(52) U.S. Cl.
CPC ............ *G06T 7/174* (2017.01); *G01N 23/04* (2013.01); *G06T 7/001* (2013.01); *H05G 1/38* (2013.01);
(Continued)

(58) Field of Classification Search
CPC .. H05G 1/00; H05G 1/02; H05G 1/08; H05G 1/26; H05G 1/28; H05G 1/30; H05G 1/38;
(Continued)

(56) References Cited

U.S. PATENT DOCUMENTS 6,556,199 B1 * 4/2003 Fang ...................... G06T 15/005
345/424
7,826,585 B2 11/2010 Proksa et al.
(Continued)

FOREIGN PATENT DOCUMENTS

WO 2008021661 2/2008

OTHER PUBLICATIONS

Blumensath, Thomas. "Compressed Sensing with Nonlinear Observations and Related Nonlinear Optimization Problems", (Jun. 2013), IEEE Transactions on Information Theory, vol. 59, No. 6, pp. 3466-3474 (Year: 2013).*

(Continued)

*Primary Examiner* — Anastasia Midkiff
(74) *Attorney, Agent, or Firm* — Ryan Alley, IP (57) ABSTRACT

An x-ray imaging system and method for reconstructing three-dimensional images of a region of interest from spatially and temporally overlapping x-rays using novel reconstruction techniques are provided. The x-ray imaging system may include a detector to generate a signal in response to x-rays incident upon the detector, wherein the signal indicates the intensity of the x-rays incident upon a pixel of the detector, a plurality of x-ray sources arranged to emit x-rays such that said x-rays pass through a region of interest (ROI) and spatially and temporally overlap at the pixel of the detector, and a processing unit to receive the signal indicating the intensity of x-rays incident upon the pixel of the detector and generate an estimate of the intensity attributable to each of the two or more x-rays overlapping at the pixel of the detector.

20 Claims, 4 Drawing Sheets

Related U.S. Application Data a continuation of application No. 15/231,039, filed on Aug. 8, 2016, now abandoned.

(51) Int. Cl.
  *H05G 1/38* (2006.01)
  *G01N 23/04* (2018.01)
  *G01N 23/10* (2018.01)

(52) U.S. Cl.
  CPC ......... *G01N 23/10* (2013.01); *G01N 2223/20* (2013.01); *G01N 2223/401* (2013.01); *G06T 2200/08* (2013.01)

(58) Field of Classification Search
  CPC .. H05G 1/56; H05G 1/60; H05G 1/64; H05G 1/70; G01N 23/00; G01N 23/02; G01N 23/04; G01N 23/043; G01N 23/046; G01N 23/06; G01N 23/083; G01N 23/10; G01N 23/18; G01N 2291/00; G01N 2291/01; G01N 2291/02; G01N 2291/04; G01N 2291/048; G01N 2291/056; G01N 2291/269; G01N 2223/00; G01N 2223/03; G01N 2223/04; G01N 2223/20; G01N 2223/30; G01N 2223/302; G01N 2223/304; G01N 2223/306; G01N 2223/308; G01N 2223/32; G01N 2223/321; G01N 2223/33; G01N 2223/3301; G01N 2223/3307; G01N 2223/3308; G01N 2223/345; G01N 2223/40; G01N 2223/401; G01N 2223/402; G01N 2223/41; G01N 2223/419; G01N 2223/42; G01N 2223/425; G01N 2223/427; G01N 2223/60; G01N 2223/639; G01N 2223/643; H01J 37/00; H01J 37/02; H01J 37/023; H01J 37/04; H01J 37/06; H01J 37/073; H01J 37/147; H01J 37/20; H01J 37/24; G01T 1/00; G01T 1/16; G01T 1/24; G01T 1/29; G01T 1/2964; G01T 1/2971; G01T 1/2985; G01T 7/00; G01T 7/08; G06T 1/00; G06T 1/0007; G06T 7/00; G06T 7/0002; G06T 7/0004; G06T 7/001; G06T 7/168; G06T 7/174; G06T 7/50; G06T 7/55; G06T 7/60; G06T 15/00; G06T 15/005; G06T 15/06; G06T 15/08; G06T 17/00; G06T 2200/00; G06T 2200/04; G06T 2200/08; G06T 2200/21; G06T 2200/28; G06T 2207/00; G06T 2207/10; G06T 2207/10072; G06T 2207/10076; G06T 2207/10081; G06T 2207/10116; G06T 2207/20; G06T 2207/30; G06T 2207/30108; G06T 2207/30112

See application file for complete search history.

(56) References Cited

U.S. PATENT DOCUMENTS

| | | | |
|---|---|---|---|
| 8,958,526 B2* | 2/2015 | Morton | G01T 1/2985 378/57 |
| 2005/0151735 A1* | 7/2005 | Boekhorst | G06T 15/06 345/424 |
| 2010/0124310 A1 | 5/2010 | Pelc et al. | |
| 2011/0188724 A1 | 8/2011 | Bruder et al. | |
| 2011/0280367 A1 | 11/2011 | Baeumer et al. | |
| 2011/0282181 A1 | 11/2011 | Wang et al. | |
| 2012/0051510 A1 | 3/2012 | Ohta et al. | |
| 2014/0176545 A1* | 6/2014 | Laine | G06T 11/40 345/424 |

OTHER PUBLICATIONS

WIPO, International Search Report and Written Opinion in corresponding PCT application PCT/GB2017/052128, dated Oct. 7, 2017.

\* cited by examiner

METHOD AND SYSTEM FOR RECONSTRUCTING 3-DIMENSIONAL IMAGES FROM SPATIALLY AND TEMPORALLY OVERLAPPING X-RAYS

RELATED APPLICATIONS

This application claims priority under 35 U.S.C. § 120 to, and is a continuation of, co-pending International Application PCT/GB2017/052128, filed Jul. 19, 2017 and designating the US, which claims priority to U.S. application Ser. No. 15/231,039, filed Aug. 8, 2016, such US Application also being claimed priority to under 35 U.S.C. § 120. These US and International applications are incorporated by reference herein in their entireties.

BACKGROUND

Field

The present disclosure generally relates to x-ray imaging, and more particularly to a method and system for reconstructing three-dimensional images from spatially and temporally overlapping x-rays.

Three-dimensional image reconstruction from x-ray projections is an important image reconstruction problem with applications in, among other things, medical imaging, industrial inspection, and airport security. Traditional x-ray imaging is most commonly based on planar radiography. This approach utilizes a single, point-like x-ray source made up of a set of vacuum-tubes arranged to generate a single cone or fan beam of x-rays over a wide range of energies and currents. However, the imaging geometries possible with such point-like x-ray sources are limited, in particular because the x-ray source must be placed a significant distance from the object (or person) to be imaged to ensure the x-ray covers a sufficient area.

In traditional x-ray systems, the large distance between the source and the object—usually called the Source to Object Distance ("SOD") or stand-off distance—requires a lot of power. To provide this power, traditional x-ray systems use large, expensive, and heavy (in the tens of kilograms) power-supplies that often require cooling, further adding to the bulk and weight of the system.

In addition, planar radiography as the name suggests is only arranged to generate two-dimensional images. X-ray tomography, or imaging by sections, may be employed to generate three-dimensional images. Typically, x-ray tomography involves taking multiple images of a stationary object or person from a variety of directions, and then using these multiple, two-dimensional images to reconstruct a three-dimensional image. Usually, a mechanical gantry is needed to move the single x-ray source (vacuum tubes) along a sequence of locations, which adds to the size and expense of the x-ray system. Also, because the images are taken sequentially, this setup requires a longer overall image capture time than would otherwise be desirable.

To minimize image capture time, multiple vacuum-tube sources may be placed at fixed or stationary locations around an object or person, with each source being selectively activated. This configuration allows for a shorter overall period of image capture; however, this system is not practical due to the cost of the sources and its relative bulk. In addition, because of the relatively large size of each vacuum-tube source, such a system can accommodate only a limited number of viewing angles. In other words, because of the size of the sources an object or person can be imaged from only a limited number of directions, which impedes the ability to generate high-resolution three-dimensional images.

An alternative to these approaches is to produce multiple x-ray sources from a single, distributed source in an emitter array. Field Enhanced Emitter ("FEE") arrays, (sometimes referred to as Field Emitter Arrays), such as Spindt arrays, may be used in x-ray tubes and serve as an advanced cathode. At high voltages, an FEE array of moderate field enhancement tips (e.g., sharp molybdenum tips or cones) may operate as emitters for x-ray production, where the individual tips (or sets of tips) can be selected to emit x-rays and thus act as an x-ray source. Similarly, cathodes produced from carbon nanotubes (CNTs) may allow for control of electron emission at low voltages, thus allowing individual CNTs to be selected to emit x-rays. In all cases, such FEE arrays allow for multiple sources of x-rays to be generated from a distributed source.

Distributed source arrays (also known as emitter arrays) allow objects to be imaged from different viewing angles by selectively activating the various individual emitters (e.g., the molybdenum tips, CNTs, etc.). Thus, distributed source arrays eliminate the need to move a heavy, vacuum tube-based source around an object or person, or the need to employ multiple such vacuum tube-based sources. For example, in the case of a flat-panel emitter array, the size of the arrays can be large and allow for significant displacement from one source (e.g., a first emitter element) on one corner of the array to a second source (e.g., a second emitter element) on the opposite corner. By activating the sources, or more particularly the emitter elements, positioned throughout the array, images may be simultaneously obtained from different viewing angles, which minimizes image capture time as compared to single-source systems, while also allowing an object to be imaged from sufficient angles so as to allow reconstruction of a three-dimensional image.

In this way, distributed source arrays allow for tomography and tomosynthesis (high-resolution, limited-angle tomography). But they also impose severe geometric constraints on system design. Because each source or emitter in the array produces its own x-ray cone, to ensure complete coverage of an object—or a region of interest ("ROI") within an object—there must be a certain amount of spatial overlap of the cones. However, such spatial overlap, and in particular x-ray overlap at a detector, may cause the images formed using such arrays to include multiple images or shadows due to the illumination of features of the object from multiple angles.

Conventional reconstruction methods cannot adequately separate spatiotemporal x-ray overlap. Therefore, in conventional systems without spatiotemporal overlap of x-rays SOD has to be kept in a narrow range to achieve the required image resolution. This correlation can be expressed as:

$$\frac{d_{max}M}{4-M} \leq \delta \leq \frac{4d_{max}}{4-M},$$

here M is a design parameter that regulates the achievable image resolution, taking values between 1 and 4 (e.g., M=2), $d_{max}$ is the maximal thickness of an object that can be imaged to the specified resolution with the given system design, and δ is the SOD. The larger the value of M, the higher the achievable image resolution, but the more constrained the SOD. Since pitch distance and collimation angle of a given source are a function of $d_{max}$ and M, such restrictions severely limit source and detector geometries. Among other things, this restriction makes it necessary to produce different emitter array panel geometries to image different body parts.

Therefore, using conventional approaches for image reconstruction, an x-ray imaging system has to be designed such that no x-rays simultaneously overlap at a detector. This limitation is attributable to, among other things, the fact that measurements from overlapping x-rays are not linear, and conventional reconstruction methods, such as linear compressed sensing, are unable to properly handle non-linear constraints, such as those produced by x-ray overlap. Because of these limitations conventional approaches to x-ray image reconstruction teach away from systems designed with spatiotemporal x-ray overlap.

Prior methods of addressing overlap have included the use of anti-scatter grids, which serve to limit the acceptance angle of x-rays to the detector, and thus prevent overlap. But anti-scatter grids also limit the information available for a given exposure by limiting the area covered by the x-rays. Alternatively, by selectively activating emitters, it is possible to fully cover an object without having x-ray overlap at the detector. However, avoiding spatial overlap with a distributed source array means either each source has to cover the entire area of interest, which increases the power requirements, or that the image takes longer to acquire as only certain non-overlapping emitter elements can be activated at the same time. The latter is of particular concern, especially in the case of children and injured patients, both of which may have a tendency to move during scans.

Accordingly, there is a need in the art for an x-ray imaging system and method that allow for more flexible imaging geometries, including greater flexibility in the selection of the distance between sources (or emitter elements) and the detector and size of the collimation angle(s). There is also a need for a system and method arranged to generate accurate three-dimensional images, while also minimizing the time needed for image capture as compared to conventional systems. Moreover, there is a need for a system and method arranged to adequately handle spatiotemporally overlapping x-rays.

SUMMARY

Embodiments of the present disclosure are directed to systems, methods, and techniques for reconstructing three-dimensional images from spatially and temporally overlapping x-rays.

In a first aspect, there is provided an x-ray imaging system, comprising a detector arranged to generate a signal in response to x-rays incident upon the detector, wherein the signal indicates the intensity of the x-rays incident upon a pixel of the detector; a plurality of x-ray sources, wherein at least two of the plurality of x-ray sources are arranged to emit x-rays such that said x-rays pass through a region of interest (ROI) and spatially and temporally overlap at the pixel of the detector; and a processing unit arranged to receive the signal indicating the intensity of x-rays incident upon the pixel of the detector and generate an estimate of the intensity attributable to each of the two or more x-rays overlapping at the pixel of the detector.

The spatiotemporal overlap of x-rays may be intentionally created at a detector in a controlled manner. Novel reconstruction techniques may then be used to reconstruct accurate three-dimensional images of an imaged object, person, or ROI using, at least in part, measurements attributable to the overlapping x-rays.

The processing unit may be further arranged to generate a three-dimensional representation of the ROI using one or more estimates of the intensity attributable to each of the two or more x-rays overlapping at the pixel of the detector.

The system may further comprise a display operably coupled to the processing unit, wherein the display is arranged to display one or more two-dimensional views of the three-dimensional representation of the ROI.

The plurality of x-ray sources may comprise two or more emitter elements of a distributed source array. The processing unit may be further arranged to voxelize the ROI into a plurality of three-dimensional, non-overlapping voxels; estimate an attenuation coefficient attributable to each said voxel; and re-voxelize the ROI into a plurality of three-dimensional, non-overlapping voxels based on the estimated attenuation coefficients attributable to each said voxel.

The processing unit may be further arranged to repeat said re-voxelization until a stopping criterion is met. The processing unit may be further arranged to estimate said attenuation coefficient attributable to each voxel using a compressed sensing algorithm.

The compressed sensing algorithm may comprise at least one of an optimization and linearization algorithm, forward-backward splitting algorithm, or combination thereof, applied to the estimated attenuation coefficients.

The plurality of x-ray sources and the detector may each include one or more sensors arranged to determine the relative positions of the x-ray sources and the detector.

The system may further comprise a controller for operating the x-ray imaging system, wherein the controller is arranged to activate a subset of the plurality of x-ray sources.

The detector may be arranged to generate electronic signals in response to x-rays. The signals may vary depending on the intensity of the x-rays at the detector, thus providing a measure of the attenuation (e.g., absorption or weakening of x-ray intensity) caused by an object or person. The x-ray imaging system may also include multiple sources of x-ray radiation. At least two of these sources may emit x-rays such that the x-rays pass through an object or person, and then spatially and temporally overlap at a pixel of the detector.

In one example, the x-ray sources may comprise discrete emitter elements in a distributed source array. The processing unit that receives the signals from the detector, including signals attributable to overlapping x-rays, may be arranged to employ novel reconstruction techniques to estimate the intensity attributable to each of the x-rays overlapping at the detector and to generate an accurate three-dimensional reconstruction of a ROI of the imaged object or person. As understood by one of skill in the art, a pixel represents a discrete element or sensor within a detector which is arranged to produce a signal that may be distinguished from other elements of the detector.

In a second aspect, there is provided a method of reconstructing an x-ray image comprising; activating two or more sources to emit x-rays such that said x-rays are delivered to a region of interest (ROI) and spatially and temporally overlap at a pixel of the detector; detecting the intensity of the overlapping x-rays incident upon the pixel of the detector; and generating an estimate of the intensity attributable to each of the two or more x-rays overlapping at the pixel of the detector using the aggregate intensity of the overlapping x-rays incident upon the pixel of the detector.

Embodiments of the present disclosure may also include a method for reconstructing a three-dimensional image from spatially and temporally overlapping x-rays. In accordance with such a method, two or more sources of x-ray radiation may be made to emit x-rays such that the x-rays are delivered through an object or person, or more specifically an ROI, and spatiotemporally overlap at a detector. The intensity of the overlapping x-rays incident upon the detector may then be detected, thus providing a measure of the attenuation caused by the object or person. The intensity attributable to each of the x-rays overlapping at the detector may then be estimated, and a three-dimensional image of a ROI of the imaged object or person generated. Novel reconstruction techniques may be employed to estimates the intensity of each overlapping x-ray.

The method may further comprise generating a three-dimensional representation of the ROI utilizing one or more estimates of the intensity attributable to each of the two or more x-rays overlapping at the pixel of the detector.

The method may further comprise displaying one or more two-dimensional views of the three-dimensional representation of the ROI.

The method may further comprise voxelizing the ROI into a plurality of three-dimensional, non-overlapping voxels; estimating an attenuation coefficient attributable to each said voxel; and re-voxelizing the ROI into a plurality of three-dimensional, non-overlapping voxels based on the estimated attenuation coefficients attributable to each said voxel.

The method may further repeat said re-voxelization until a stopping criterion is met.

The method may further comprise using a compressed sensing algorithm to estimate said attenuation coefficient attributable to each voxel.

The compressed sensing algorithm may comprise at least one of an optimization and linearization algorithm, forward-backward splitting algorithm, or combination thereof.

The method may further comprise performing a calibration comprising the steps of activating each source to emit x-rays one at a time; and activating sets of sources to emit x-rays such that said x-rays overlap at the pixel of the detector.

The method may further comprise selecting the two or more sources to activate to emit x-rays so as to optimize at least one of image acquisition speed, image quality, and ROI coverage.

The methods described herein may be undertaken using the system of the first aspect.

The phrase "arranged to" may be understood as meaning "capable of".

Various objects, features, embodiments, and advantages of the present invention(s) will become more apparent from the following detailed description of embodiments of the present disclosure, along with the accompanying drawings. The present Summary, while providing an introduction to various embodiments, is not intended to limit the scope of the subject matter to be claimed. Further advantages of the present invention(s) will be apparent to a person of skill in the art in view of the foregoing disclosure.

The present invention will be described with respect to certain drawings but the invention is not limited thereto but only by the claims. The drawings described are only schematic and are non-limiting. Each drawing may not include all of the features of the invention and therefore should not necessarily be considered to be an embodiment of the invention. In the drawings, the size of some of the elements may be exaggerated and not drawn to scale for illustrative purposes. The dimensions and the relative dimensions do not correspond to actual reductions to practice of the invention.

Furthermore, the terms first, second, third and the like in the description and in the claims, are used for distinguishing between similar elements and not necessarily for describing a sequence, either temporally, spatially, in ranking or in any other manner. It is to be understood that the terms so used are interchangeable under appropriate circumstances and that operation is capable in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that operation is capable in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Similarly, it is to be noticed that the term "connected", used in the description, should not be interpreted as being restricted to direct connections only. Thus, the scope of the expression "a device A connected to a device B" should not be limited to devices or systems wherein an output of device A is directly connected to an input of device B. It means that there exists a path between an output of A and an input of B which may be a path including other devices or means. "Connected" may mean that two or more elements are either in direct physical or electrical contact, or that two or more elements are not in direct contact with each other but yet still co-operate or interact with each other. For instance, wireless connectivity is contemplated.

Reference throughout this specification to "an embodiment" or "an aspect" means that a particular feature, structure or characteristic described in connection with the embodiment or aspect is included in at least one embodiment or aspect of the present invention. Thus, appearances of the phrases "in one embodiment", "in an embodiment", or "in an aspect" in various places throughout this specification are not necessarily all referring to the same embodiment or aspect, but may refer to different embodiments or aspects. Furthermore, the particular features, structures or characteristics of any embodiment or aspect of the invention may be combined in any suitable manner, as would be apparent to one of ordinary skill in the art from this disclosure, in one or more embodiments or aspects.

Similarly, it should be appreciated that in the description various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Moreover, the description of any individual drawing or aspect should not necessarily be considered to be an embodiment of the invention. Rather, as the following claims reflect, inventive aspects lie in fewer than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some features included in other embodiments, combinations of features of different embodiments are meant to be within the scope of the invention, and form yet further embodiments, as will be understood by those skilled in the art. For example, in the following claims, any of the claimed embodiments can be used in any combination.

In the description provided herein, numerous specific details are set forth. However, it is understood that embodiments of the invention may be practised without these specific details. In other instances, well-known methods, structures and techniques have not been shown in detail in order not to obscure an understanding of this description.

In the discussion of the invention, unless stated to the contrary, the disclosure of alternative values for the upper or lower limit of the permitted range of a parameter, coupled with an indication that one of said values is more highly preferred than the other, is to be construed as an implied statement that each intermediate value of said parameter, lying between the more preferred and the less preferred of said alternatives, is itself preferred to said less preferred value and also to each value lying between said less preferred value and said intermediate value.

The use of the term "at least one" may mean only one in certain circumstances. The use of the term "any" may mean "all" and/or "each" in certain circumstances.

The principles of the invention will now be described by a detailed description of at least one drawing relating to exemplary features of the invention. It is clear that other arrangements can be configured according to the knowledge of persons skilled in the art without departing from the underlying concept or technical teaching of the invention, the invention being limited only by the terms of the appended claims.

DETAILED DESCRIPTION

Figure 1:
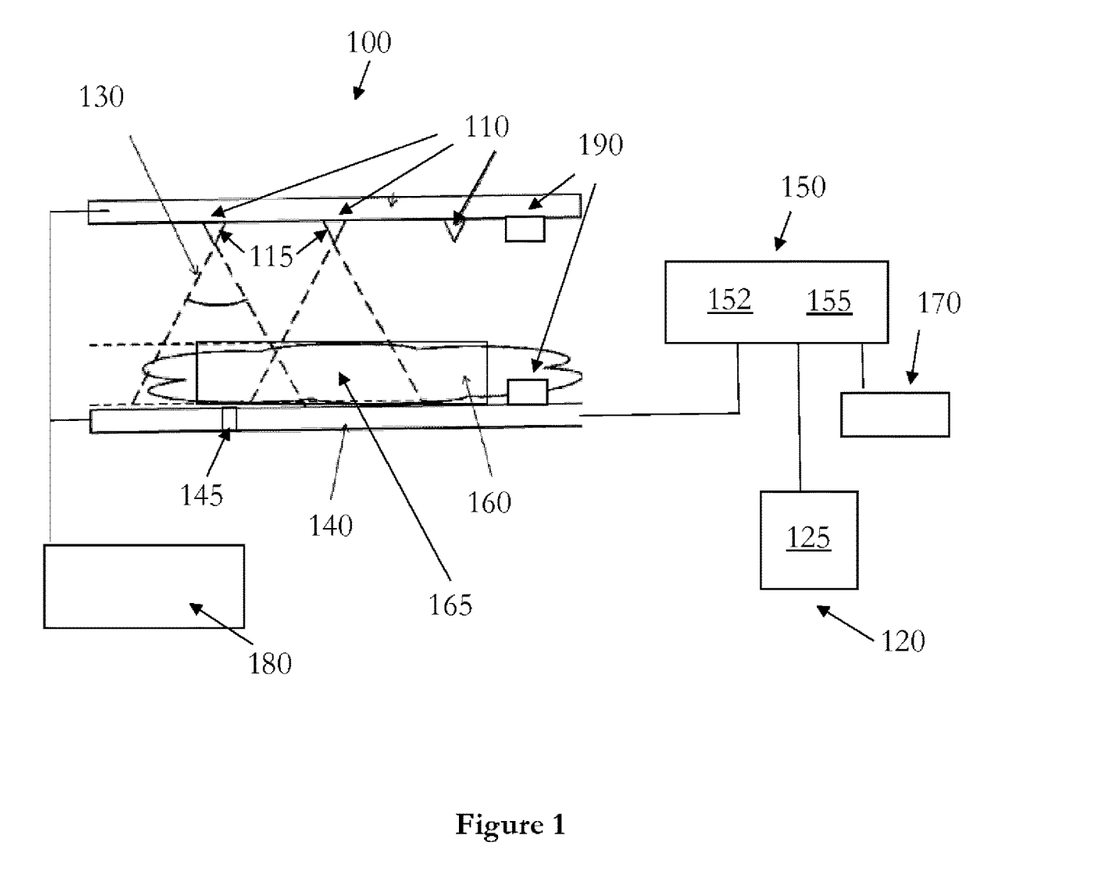
FIG. 1 is a schematic, cross-sectional representation of an example of an x-ray imaging system in accordance with aspects of the present disclosure.

FIG. 1 shows an example of an x-ray imaging system 100 in accordance with aspects of the present disclosure. As illustrated, x-ray imaging system 100 may include two or more sources 110 of x-ray radiation, such as two or more emitter elements of a distributed source array.

A collimator (not shown) may be positioned adjacent to each source 110, and may be used to define the size and shape of each x-ray radiation beam 130 emitted by each source 110. In typical use, x-ray beam 130 may be conical in shape, thus forming a conelet. Alternatively, source 110 may emit various other shapes of x-ray beam 130. A "conelet" may refer to the generally conical envelope of the x-ray emission from a single emitter. The term may be used to distinguish the emission of a single emitter from that of the overall array of emitters.

Figure 2:
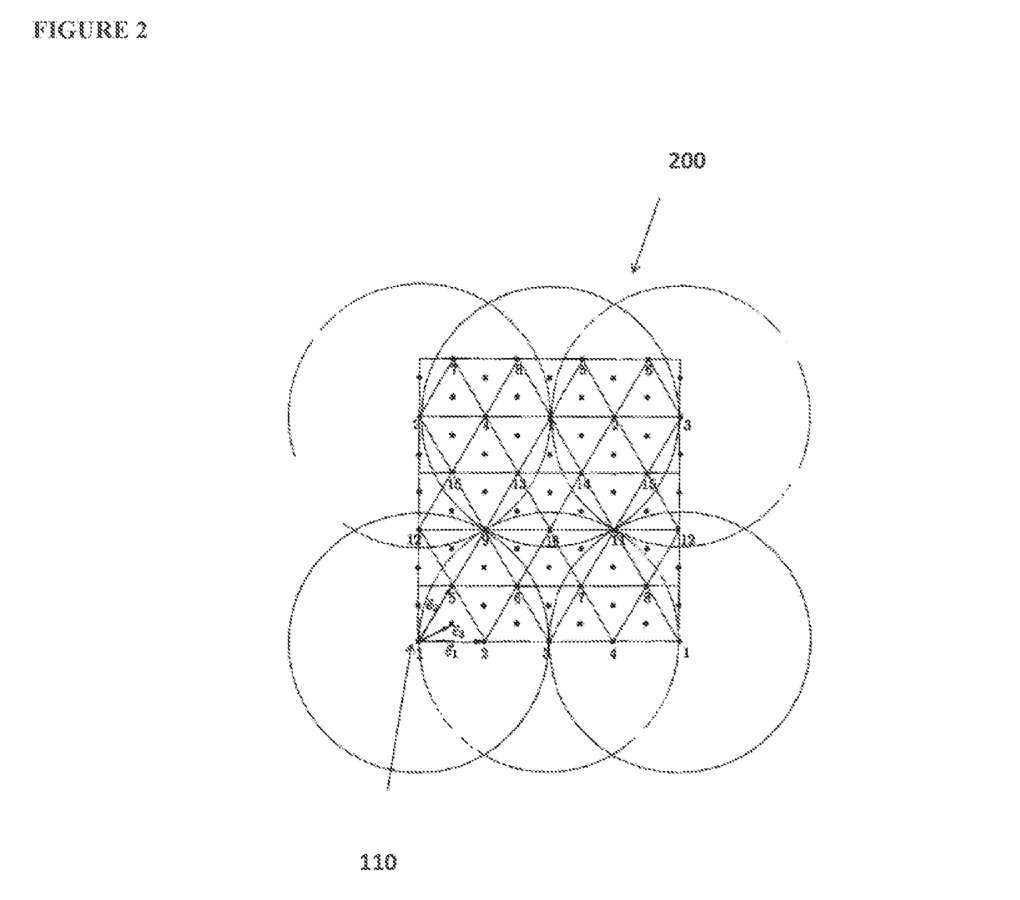
FIG. 2 is a schematic plan-view representation of an emitter array in accordance with aspects of the present disclosure.

Referring to FIG. 2, in certain embodiments of the present disclosure, sources 110 may form part of a distributed source array, such as an FEE. In one example, distributed source array 200 may include a plurality of separate and discrete emitter elements, wherein each emitter element is a source 110 of x-ray radiation. As illustrated, each source 110 may be arranged with its center at node points of a grid of equilateral triangles, thus each source 110 may be equally spaced (vertically and horizontally) throughout emitter array 200. Alternatively, sources 110 may be arranged in various other configurations (e.g., spaced farther apart on the x-axis than on the y-axis, composed of various grid patterns, such as squares, rectangles, or hexagons, or distributed randomly or pseudo-randomly).

X-ray imaging system 100 may also include one or more detectors 140, which may include pixels 145 that produce an electrical signal that represents the intensity of impinging x-ray beams 130 on detector 140, and hence provide a measure of the attenuation (e.g., absorption or weakening of x-ray intensity) attributable to object 160. As discussed herein, because these electrical signals provide a measure of attenuation attributable to the scanned portions of object 160, they may be processed to generate three-dimensional reconstructions 155 of a ROI 165 of object 160. In an embodiment of the present disclosure, detector 140 may be formed from a plurality of detector pixels 145 (or sensing diodes), each of which may be arranged to produce an electrical signal that represents the intensity of impinging x-ray beam 130.

As is illustrated in FIG. 1, x-ray imaging system 100 may be configured so that, when in use, at least one exposure or scan of a ROI 165 involves the spatiotemporal overlap at detector 140 of x-ray beams 130 emitted from at least two different sources 110. This configuration may be achieved in various ways. For example, controller 180 may be operably coupled to sources 110, and thus used to selectively activate a subset 115 of sources 110. In one aspect, controller 180 may be configured to control the power provided to each individual source 110. In this way, controller 180 may be able to provide emission point activation, making it possible to activate a subset 115 of sources 110 to emit x-ray beams 130, and also making it possible to select overlapping sources 110.

X-ray imaging system 100 may also include processing unit 150. Processing unit 150 may comprise one or more processors, computers, CPUs, or similar devices, and may be configured to process image information, such as the intensity of x-ray beams 130 incident on detector 140. For example, processing unit 150 may be operably coupled to detector 140, so as to receive data from detector 140, such as electronic signals corresponding to the intensity of impinging x-ray beams 130 on detector 140.

Processing unit 150 may also be configured to implement one or more process(es) (as described herein) to deconvolve the jointly measured attenuation attributable to the spatiotemporal overlap of x-ray beams 130 at detector 140. By knowing the relative locations 500 of sources 110 and detector 140, such as the positions of each source 110 activated in a given exposure and the portion of the detector 140 (e.g., the detector pixel 145) from which an electronic signal representing the intensity of the x-ray beams 130 is received, processing unit 150 may convert the electronic signals received from detector 140 into a three-dimensional data array 155 representing the attenuation at various points throughout the ROI 165.

In an aspect of the present disclosure, processing unit 150 may subdivide object 160, or more specifically the ROI 165 of object 160, into three-dimensional, non-overlapping volume elements, or voxels 152. Processing unit 150 may then model each voxel 152 as being occupied by part of object 160, and as being made up of homogenous material whose attenuation coefficient (which characterizes how easily x-rays pass through the material within the voxel 152) represents a single data point. Processing unit 150 may then collect all such data points in an array called a vector.

Processing unit 150 may compare the modeled vector to the electronic signals received from detector 140 corresponding to the intensity of the impinging x-ray beams 130 on detector 140. In this way, processing unit 150 may compare the modeled attenuation of each voxel 152 to the detected attenuation attributable to each voxel 152. Processing unit 150 may then utilize reconstruction algorithms based on compressed sensing methods to iteratively refine the modeled vector based on the actual measurements, and in turn, may use the results of such iterations to reconstruct a three-dimensional model 155 of the ROI 165.

Referring to FIG. 1, x-ray imaging system 100 may also include memory 170. Memory 170 may be part of processing unit 150, or alternatively, may be operably coupled to processing unit 150. Memory 170 may store, for later processing by processing unit 150, data acquired during one or more x-ray scans. For example, in typical use, an object or patient may be exposed to a short sequence of x-ray exposures (1-50 exposures, for example, 5-10 exposures), and data from these exposures, such as the attenuation measured during each exposure, may be stored in memory 170, and subsequently processed or used to refine image reconstruction as discussed herein.

As noted, in order to determine the attenuation attributable to the portions of an ROI 165 of object 160, the relative position 500 (distance and orientation) of each source 110 and detector 140, or detector pixel 145, must be known. In the case of fixed installations, the required measurements may be made at the time of installation, and verified during routine maintenance. Alternatively, the relative position 500 may be determined in any number of other ways, including via mechanical measurement.

In an aspect of the present disclosure, x-ray imaging system 100 may include one or more sensors 190 arranged to determine the relative position(s) 500 of sources 110 to detector 140, and/or vice versa. Sensors 190 may be any type of proximity sensor that may be used to determine the distance between each source 110 and detector 140. This distance may be used to select a suitable subset 115 of sources 110 to use when imaging object 160. For example, an operator or radiographer may utilize controller 180 to select a ROI 165 of object 160. In an aspect of the present disclosure, a range of SODs may then be pre-calculated (e.g., by processing unit 150) and provided to the operator based on the fixed pitch and collimation angle(s) of the manufactured sources 110 and the ROI 165 to be imaged. The operator or radiographer may place detector 140 within the specified range of SODs. Sensors 190 may then measure the distance between sources 110 and detector 140 (or alternatively between source 110 and object 160), and a subset 115 of sources 110, including two or more sources 110 that will spatiotemporally overlap at one or more pixels 145 of detector 140, may be calculated (e.g., by processing unit 150) that optimize image acquisition speed, image quality, and/or ROI 165 coverage. For purposes of the present disclosure, spatial and temporal overlap (or spatiotemporal overlap) may include the case where two or more X-rays are incident on a pixel 145 of a detector within a sampling time interval.

X-ray imaging system 100 may also include a visualization workstation and display 120. Visualization workstation and display 120 may be operably coupled to processing unit 150, and may be used to observe reconstructed three-dimensional images 155 of an ROI 165 of object 160. For example, visualization workstation 120 may perform calculations to transform the three-dimensional data array determined by processing unit 150 into one or more internal views (e.g., two-dimensional slices) 125 of the ROI 165 that may be displayed to an operator or radiographer.

Figure 3:
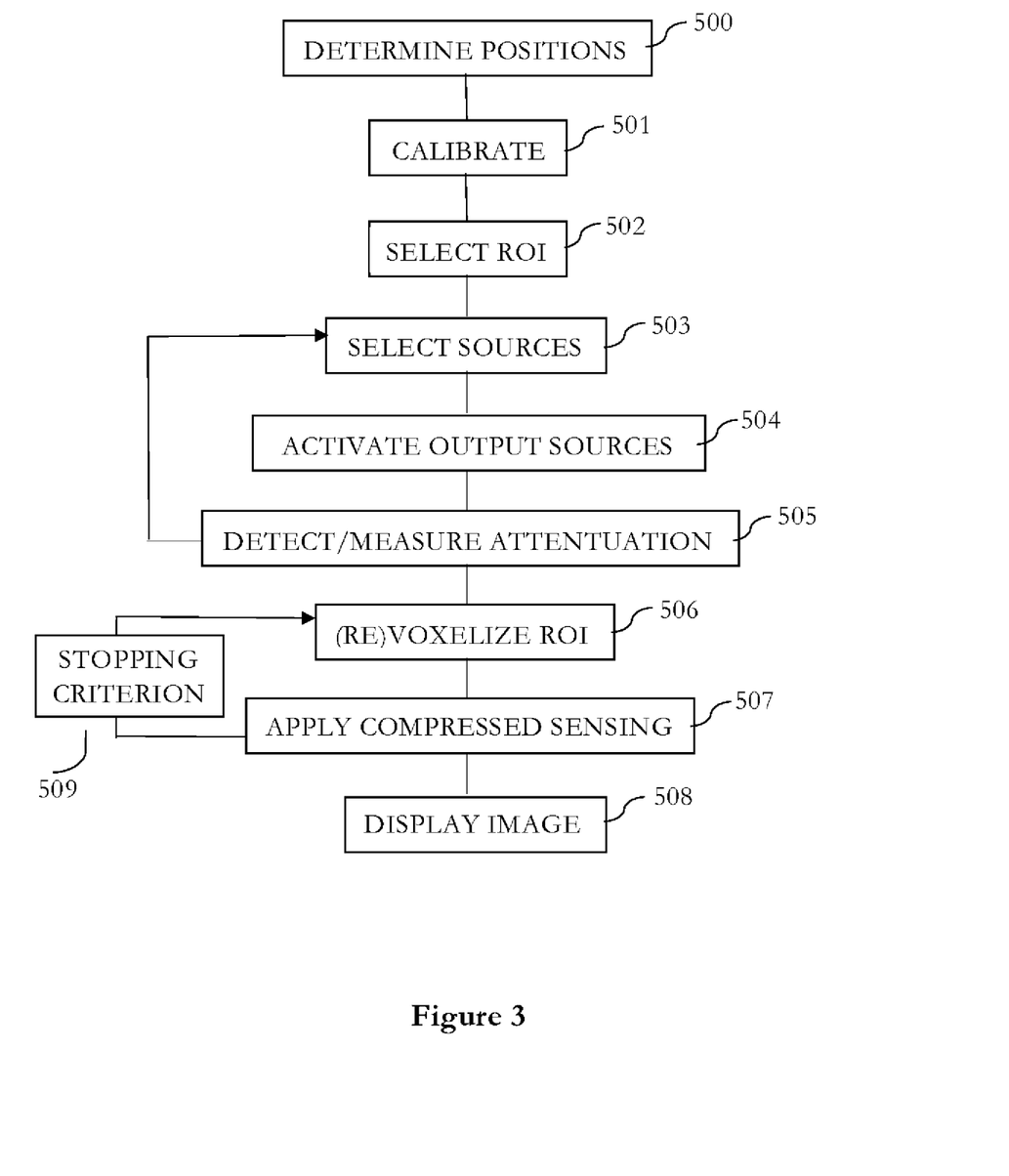
FIG. 3 is a flow chart illustrating an exemplary method of reconstructing an x-ray image in accordance with aspects of the present disclosure.

FIG. 3 is a flow chart illustrating an exemplary method of reconstructing an x-ray image in accordance with aspects of the present disclosure. The method may begin at step 501, wherein a calibration procedure, such as an air calibration (or air shots), may be performed as a means to offset air attenuation, spatial variation of each source 110, detector 140 sensitivity variation, and to compensate for faulty pixels 145 of detector 140, and so forth. Calibration data may further be used to understand, and if necessary compensate for, non-linearity in detector 140 response; conventional digital detectors are linear (e.g., twice the input flux produces twice the signal output), but when the angles of incidence are different this may no longer be true.

In an aspect of the present disclosure, a two-step calibration may be performed whereby each source 110 may be activated one at a time, and then subsequently sources 110 may be activated in groups or sets wherein at least two x-ray beams 130 spatiotemporally overlap at detector 140. While such a two-step calibration cannot account for all possible potential variations, it does allow for the offset of primary response issues in a given context.

This calibration may be performed as the first step of the method illustrated in FIG. 3 (e.g., prior to step 502). Alternatively, such calibrations need not be performed immediately prior to the implementation of the method illustrated in FIG. 3, and may instead be performed on a periodic basis (e.g., daily or weekly) to capture performance variations (e.g., due to temperature) or decay (e.g., due to aging, x-ray exposure or physical damage). The calibration results may be used to adjust the reconstruction algorithms described herein, and the data from such calibrations may be stored in memory 170 and later processed by processing unit 150.

With reference to FIG. 3, assuming the calibration results are within acceptable limits and any configuration changes or revised measurements have been recorded, one or more data acquisition procedures may be performed (steps 502-505). As an initial matter, a three-dimensional ROI 165 of object (or person) 160 may be selected at step 502. This selection may be performed by an operator or radiographer using controller 180, or alternatively, in any number of ways, as would be understood by a person of skill in the art in view of the present disclosure. Based on the selected ROI 165, pitch and collimation angle(s) of sources 110, and the SOD, a group or subset 115 of sources 110 to be used for imaging the ROI 165 may be selected at step 503. Geometric calculations that take ROI 165 geometry, pitch and collimation angle(s), and the SOD into account may be employed to optimize one or more of the image acquisition speed, the image quality, and/or ROI 165 coverage.

Although not illustrated, in one aspect of the present disclosure a range of SODs may be calculated based on the fixed pitch and collimation angle(s) of the manufactured sources 110, and provided to an operator or radiographer. The operator may then place object 160 within the calculated range of SODs, between sources 110 and detector 140. The distance between sources 110 and detector 140 may then be measured by, for example, sensor(s) 190, or mechanically. Alternatively, sources 110 and detector 140 may be kept stationary, or if mobile may be designed to move in such a way that their relative positions 500 are known at all times throughout the x-ray scanning process (e.g., sources 110 and/or detector 140 may move in known pattern).

At step 504, the group or subset 115 of sources 110 selected at step 503 may be activated, and the selected ROI 165 (step 502) may be exposed to a sequence of x-ray exposures. The local variations in intensity of impinging x-ray beams 130 on detector 140 (after passing through object 160) may then be measured at step 505, thus providing a measure of the attenuation attributable to object 160. The attenuation measured at step 505 may be stored, for example, in memory 170 or, alternatively, at processing unit 150. These attenuation measurements may be appended to attenuation measurements obtained from previous scans (e.g., from previous activation of a group or subset 115 of sources 110). This process may be repeated until sufficient raw data has been captured to permit conversion of the data into a desired image of the ROI 165.

Next with reference to blocks 506 through 507, an iterative reconstruction process may be implemented to reconstruct a three-dimensional representation 155 of the ROI 165 of object 160, repeated until a stopping criterion 509 is met. The ROI 165 may then be subdivided (step 506) into n three-dimensional, non-overlapping volume elements called voxels 152. The process of defining (or re-defining) such voxels 152 may be referred to as voxelization (or re-voxelization). Each voxel may be modeled as having homogenous radiation absorption properties (e.g., same attenuation coefficient) throughout. In this way, each voxel 152 may represent a single sample or data point (e.g., a single attenuation coefficient). All such data points may be collected in an array called a vector. This voxelization process may be performed by processing unit 150, or alternatively, by any other number of means, as would be understood by a person of skill in the art in view of the present disclosure.

Compressed sensing methodologies, as discussed herein, arranged to determine the intensity attributable to each of two or more spatiotemporally overlapping x-ray beams may be used to determine a set of attenuation coefficients which best fit the available data obtained at step 505. In this way, a suitable voxelization may then be determined by iteratively refining the voxelization (repeating steps 506 and 507) until a stopping criterion 509 is satisfied, such as achieving a predetermined optimality condition (e.g., a desired resolution). Because the compressed sensing methodologies used to determine the attenuation coefficients for a particular voxelization typically involve one or more iterations, for ease of reference, each successive refinement of the voxelization may be referred to as an outer iteration, while each successive iteration of the compressed sensing methodology (within each particular voxelization) may referred to as an inner iteration.

With reference to block 507, after voxelization (or re-voxelization), compressed sensing methods may be used to deconvolve intensity measurements attributable to spatiotemporally overlapping x-rays, and thus determine the attenuation, or more precisely attenuation coefficient, attributable to the material occupying each voxel 152. Compressed sensing is a mathematical technique that exploits the sparsity in an image to allow reconstruction from fewer measurements than would otherwise be required. This technique may also be referred to as a basis pursuit problem. Conventional basis pursuit problems concern underdetermined linear systems, which have infinitely many solutions, with the aim of finding among these a solution with fewest non-zero entries. Mathematically, this concept may be expressed as:

$$\min_{x \in R^n} |\{i : x_i \neq 0\}|,$$

subject to $Ax = b$, where $|\cdot|$ denotes the cardinality, or the number of elements, of a set, A is a m×n matrix, and b a vector of size m, where m is the number of measurements, n is the number of voxels 152, and x is the vector of attenuation coefficients and $x_i$ is the attenuation coefficient of the i-th voxel 152.

In cases where two or more x-ray beams 130 from different sources 110 overlap at detector 140, measurements from such overlapping x-rays will not be linear (as they are for non-overlapping x-rays). Instead, if two x-ray beams 130 overlap at detector 140, or more specifically at a pixel 145 of detector 140, the attenuation at measurement j sums up to $$\frac{I_{D_j}}{I_{E_{j1}} + I_{E_{j2}}} = \frac{I_{E_{j1}}}{I_{E_{j1}} + I_{E_{j2}}} \exp\left(\sum_{i=1}^{n} -\xi_{ij1} x_i\right) + \frac{I_{E_{j2}}}{I_{E_{j1}} + I_{E_{j2}}} \exp\left(\sum_{i=1}^{n} -\xi_{ij2} x_i\right). \quad (1)$$

where each of the two terms on the right-hand side corresponds to the measurements attributable to one x-ray beam 140, and where $I_{E_{jk}}$ corresponds to radiation at the emitter (or source) k, $I_{D_j}$ corresponds to radiation at the detector j, and wherein $\xi_{ijk}$ denotes the distance traveled by x-ray beam 130 emanating from the k-th source 110 through the i-th voxel 152. For $p_j$ x-rays overlapping at the jth pixel 145 of detector 140 the more general formulation is $$\psi_j := \frac{I_{D_j}}{\sum_{l=1}^{p_j} I_{E_{jl}}} = \sum_{k=1}^{p_j} \frac{I_{E_{jk}}}{\sum_{l=1}^{p_j} I_{E_{jl}}} \exp\left(\sum_{i=1}^{n} -\xi_{ijk} x_i\right). \quad (2)$$

In one approach, nonlinear constraints (2) may be linearized by neglecting the nonlinearity of the measurements by assuming that for two sufficiently close positive a, b∈R and Δ in [0,1] we have $\log(\lambda a + (1-\lambda) b) \approx \lambda \log(a) + (1-\lambda) \log(b)$. In the context of overlapping x-ray beams 130, the constraints (2) are simplified to $$\psi_j \approx \exp\left(-\sum_{k=1}^{p} \lambda_{jk} \sum_{i=1}^{n} \xi_{ijk} x_i\right), \quad (3)$$

where the coefficients $$\lambda_{jk} = \frac{I_{E_{jk}}}{\sum_{l=1}^{p} I_{E_{jl}}}$$
(4)

are the weights in a convex combination, that is, they are positive and sum to 1. Applying the logarithm to the right-hand side, the following linear constraints are obtained:

$$b_j := \log(\psi_j) \approx \sum_{i=1}^{n}\left(-\sum_{k=1}^{p_j}\lambda_{jk}\xi_{ijk}\right)x_i, (j=1,\ldots,m),$$
(4)

or $Ax=b$, where b is the vector of $b_j$ and where A is a matrix consisting of a negative convex combination of distances $a_{ij} = -\sum_{k=1}^{p_j}\lambda_{jk}\xi_{ijk}$, where $p_j$ denotes the number of x-ray sources that overlap at measurement j. A can be interpreted as a compressed version of the corresponding linear measurement matrix $\tilde{A}$ arising from the sequential exposures:

$$A = \begin{pmatrix} -\sum_{k=1}^{p_1}\lambda_{1k}\xi_{11k} & \cdots & -\sum_{k=1}^{p_1}\lambda_{1k}\xi_{n1k} \\ \vdots & \ddots & \vdots \\ -\sum_{k=1}^{p_m}\lambda_{mk}\xi_{1mk} & \cdots & -\sum_{k=1}^{p_m}\lambda_{mk}\xi_{nmk} \end{pmatrix},$$

$$\tilde{A} = \begin{pmatrix} -\xi_{111} & \cdots & -\xi_{n11} \\ \vdots & \ddots & \vdots \\ -\xi_{11p_1} & \cdots & -\xi_{n1p_1} \\ -\xi_{121} & \cdots & -\xi_{n21} \\ \vdots & \ddots & \vdots \\ -\xi_{1mp_m} & \cdots & -\xi_{mnp_m} \end{pmatrix}$$
(5)

The above provides a first linear approximation of the nonlinear measurements. However, depending on the difference of attenuation along the overlapping x-ray beams 130, the two terms in (4) may differ too much to justify this simplification.

Accordingly, for each measurement j parameters $T_j$ that determine the linearization may be iteratively estimated. The corresponding model may then be optimized based on these parameters.

For two values $a_k>0$ (k=1, ..., p) and convex combination weights $\lambda_k>0$ (k=1, ..., p) such that $\sum_{k=1}^{p}\lambda_k=1$, $\tau(a,\lambda)$ is defined as the ratio $$\tau(a,\lambda) = \frac{\log\left(\sum_{k=1}^{p}\lambda_k a_k\right)}{\sum_{k=1}^{p}\lambda_k \log(a_k)}.$$
(6)

$\tau(a,\lambda)<1$ holds when all $a_k<1$, because of the concavity of the logarithmic function. By applying this concept to the measurements (3), the ratios $\tau_j(x)$ for $p_j$ overlapping x-ray cones at measurement j are given by $$\tau_j(x) = \frac{\log\left(\sum_{k=1}^{p_j}\lambda_{jk}\exp\left(\sum_{i=1}^{n}-\xi_{ijk}x_i\right)\right)}{-\sum_{i=1}^{n}\sum_{k=1}^{p_j}\lambda_{jk}\xi_{ijk}x_i}.$$
(7)

And thus, the following formulation is obtained for the constraints (2), where $b_j=\log(\psi_j)$ as before, $$\psi_j = \sum_{k=1}^{p_j}\lambda_{kj}\exp\left(\sum_{i=1}^{n}-\xi_{ijk}x_i\right)$$
(8)

$$b_j = \log\left(\sum_{k=1}^{p_j}\lambda_{kj}\exp\left(\sum_{i=1}^{n}-\xi_{ijk}x_i\right)\right)$$
(9)

$$\Leftrightarrow b_j = \tau_j \sum_{i=1}^{n} a_{ij}x_i,$$
(10)

where $a_{ij}=-\sum_{k=1}^{p_j}\lambda_{jk}\xi_{ijk}$ are the entries of matrix A. Introducing a diagonal matrix $$\tau=\text{diag}(\tau_1,\ldots,\tau_m)$$
(11)

yields the constraint $$\tau Ax=b$$
(12)

Based on the foregoing, the following reconstruction (optimization and linearization) algorithm may be formulated, wherein the set of measured x-rays may be represented in a sparse matrix A of intersection lengths of x-rays and voxels 152, in association with corresponding vector measurements b, where m (the number of measurements) may be much less than n (the number of voxels 152): Once the sparse matrix and vector measurements are assembled, the following may be solved, and iteratively refined for t=1, 2, . . . , until the vector x has sufficiently converged.

1. Update x:

$$x \leftarrow \arg\min_{x\geq 0}\|x\|_s + \frac{1}{2\mu}\|\tau Ax - b\|_2^2,$$

where $\mu>0$ is a regularization parameter that provides a balance between sparsity prior and the data fidelity term, and where the sparsity prior $\|x\|_s$ is a $L_1$-norm, the Total Variation Norm, or a convex combination of the two.

2. Update $\tau$:

$$\tau \leftarrow \text{diag}(\tau_1(x),\ldots,\tau_m(x)),$$

where $$\tau_j(x) = \frac{\log\left(\sum_{k=1}^{p_j}\lambda_{jk}\exp\left(\sum_{i=1}^{n}-\xi_{ijk}x_i\right)\right)}{-\sum_{i=1}^{n}\sum_{k=1}^{p_j}\lambda_{jk}\xi_{ijk}x_i}.$$

An initialization may be performed where the following may be computed first:

0. $x = A^T b$, $\tau = I$, where I is the m×m identity matrix.

The following describes an alternative way of solving the reconstruction problem with overlap. With reference to (2), assuming again interest in a sparse reconstruction of the vector x, minimization with L1 prior yields $$\min \|x\|_1 \text{ s.t. } \sum_{k=1}^{p_j} \lambda_{jk} \exp\left(-\sum_{i=1}^{n} \xi_{ijk} x_i\right) = \psi_j \quad (13)$$

with measurements $\psi_j = ID_j / \sum_{l=1}^{p_j} IE_{jl}$, (j=1, ..., m). The coefficients $-\xi_{ijk}$ may be represented with sparse vectors $r_{jk} \in R^n$:

$$r_{jk} = (-\xi_{1jk} \ldots -\xi_{njk})^T, (j=1, \ldots, m). \quad (14)$$

Allowing for noise in the data constraint term, the following least squares formulation of (13) is derived:

$$\min_{x \geq 0} \left\{ \|x\|_1 + \frac{1}{2\mu} \sum_{j=1}^{m} \left( \sum_{k=1}^{p_j} \lambda_{jk} \exp(r_{jk}^T x) - \psi_j \right)^2 \right\}, \quad (15)$$

with regularization parameter $\mu > 0$, which provides a balance between sparsity prior and data fidelity term. The formulation (15) corresponds to an optimization problem of the form $$\min_x \{f(x) + g(x)\} \quad (16)$$

with convex non-differentiable $f: R^n \to R$ $$f(x) = \|x\|_1, \quad (17)$$

and partially convex, differentiable $g: R^n \to R$ $$g(x) = \frac{1}{2\mu} \sum_{j=1}^{m} \left( \sum_{k=1}^{p_j} \lambda_{jk} \exp(r_{jk}^T x) - \psi_j \right)^2. \quad (18)$$

An optimization problem of form (16) may be solved using the first-order, forward-backward splitting update sequence for t=0, 1, 2 ... and $x^0 = 0$:

$$x^{t+1} = \text{prox}_{\lambda f}(x^t - \lambda \nabla g(x^t)) \quad (19)$$

with convergence rate O(1/t) and step size $\lambda = 1/L$. Update sequence (19) converges to a minimum of (16), if $f$ is a lower semi-continuous convex function, and g is convex, differentiable, and has a Lipschitz continuous gradient.

To optimize (15) as a special case of (16), the initialization for x is kept smaller than a minimizer $\hat{x}$, because g is partially convex for $x \leq \hat{x}$. Furthermore, step sizes $\lambda$ should be chosen such that $x \leq \hat{x}$ is assured for all iterations t. The step sizes $\lambda$ may be determined using a backtracking line search algorithm (e.g., $\lambda \leftarrow \lambda c$). The measurements are given with $\psi_j = \psi(\hat{x})$, where $$\psi_j(x) := \sum_{k=1}^{p_j} \lambda_{jk} \exp(r_{jk}^T x),$$

and hence the line search can be constrained by $$\psi_j(x) \leq \psi_j, \text{ for all } j=1, \ldots, m. \quad (20)$$

which is a necessary, but not sufficient, condition for $x \leq \hat{x}$.

Based on the foregoing, the following second reconstruction (forward-backward splitting) algorithm may be formulated, and used to generate a three-dimensional reconstruction 155 of the ROI 165 (or a portion of the ROI): The following may be assembled based on measurements obtained at block 505:

$\psi \in R^m$: vector of measurements $r_{jk} \in R^n$: sparse vectors of intersection lengths or rays and voxels $c, \tau \in (0, 1)$: line search control parameters $$L = \frac{1}{\mu} 2mp^2 \xi_{max}^2:$$

Lipschitz constant for g $\theta > 0$: tolerance threshold for stopping criterion Next, an initialization $x^0 = 0$ may be performed, and the following may be solved, and iteratively refined for t=1, 2, etc.:

1. Compute Search Direction:

$$\nabla g(x) = \frac{1}{\mu} \sum_{j=1}^{m} \left( \sum_{k=1}^{p_j} \lambda_{jk} \exp(r_{jk}^T x) - \psi_j \right) \left( \sum_{k=1}^{p_j} \lambda_{jk} \exp(r_{jk}^T x) r_{jk} \right).$$

2. Backtracking Line Search: $\lambda = 1/L$
do
 $\lambda \leftarrow \lambda c$
 $x^{new} = x - \lambda \nabla g$
while $g(x^{new}) - g(x) > \lambda c |\nabla g|^2$ and $\exists j \in 1, \ldots, m: \psi_j(x^{new}) > \psi_j$ 3. Update x:
$x^t = \text{prox}_{\lambda f}(\max\{0; x^{t-1} - \lambda \nabla g(x^{t-1})\})$ 4. Stopping Criterion:

$$\text{if } \frac{\|x^t - x^{t-1}\|_2}{\|x^{t-1}\|_2} < \theta : \text{stop}$$

Experimental results using both simulated and real-world measurements have shown that the reconstruction algorithms disclosed herein significantly improve reconstruction accuracies from linear constraints. Such experiments show that the present methods are arranged to recover nearly the same image quality as sequential (non-overlapping) exposures up to an average overlap of ~2, while highly increasing robustness with respect to SOD and emitter collimation angles, and increasing image capture times. In other words, the present methods provide optimal results when, on average, the spatiotemporal x-ray overlap per pixel 145 of detector 140 is attributable to two or fewer sources 110.

Because in typical use a subset of pixels of detector 140 will detect one or fewer x-ray beams 130, the present methods allow for a configuration where a second subset of pixels may detect spatiotemporally overlapping x-rays from ≥2 sources 110.

With reference again to step 507, at the conclusion of each inner iteration (e.g., solving and iteratively refining the compressed sensing algorithm), a subsequent outer iteration may be performed (step 506). In each subsequent outer iteration, each voxel 152 of the previous voxelization may be modified based on the attenuation coefficients determined at step 507. For example, to better fit the measured attenuation, voxels 152 may be further subdivided into smaller voxels, or alternatively, two or more adjacent voxels may be merged into a single voxel. An optimal voxelization may be obtained by iteratively amending the voxelization until a stopping criterion 509 is met (e.g., a desired image resolution).

At the conclusion of the iterative loop (steps 506 and 507), the resulting x (attenuation coefficient) values derived for each voxel 152 may be used to produce a three-dimensional, graphical representation 155 of the ROI object 160. This graphical representation may be displayed (step 508) as a three-dimensional image, or more typically as a set of two-dimensional "slices" (e.g., along the z-axis). In this way, the ROI 165 may be examined by the operator or radiographer.

Notably, the foregoing method, while presented in ordered steps for illustrative purposes is merely exemplary. The steps described need not be performed in the recited order. Moreover, each of the recited steps do not need to be performed to still be in keeping with the present disclosure.

As would be understood by a person of skill in the art in view of the present disclosure, embodiments described herein may overcome the design restrictions of conventional systems, because the removal of non-overlap conditions allow for more robust system configurations. For example, the relaxing of non-overlap conditions may be particularly useful in the case of tomosynthesis of thick objects. In such cases, to ensure complete x-ray coverage at the top of the object there typically will be significant overlap at the bottom of the object, due to the cone or fan shape of the x-ray beams. Because conventional system cannot handle such overlap, the top of such objects are usually undersampled (and, thus, unclear) as compared to the bottom of the object. Because embodiments of the present invention allow x-ray overlap, higher sampling can be achieved at the top of such objects, thereby producing clearer images.

In addition, in medical applications, where the total duration of consecutive exposures is limited (typically to 0.1 sec) due to patient movement, conventional systems have to strike a balance between the achievable resolution in the x-y plane (the plane of the detector) and in the z-direction (the direction orthogonal to the x-y plane). To increase the resolution in the z-direction, more obtuse collimation angles have to be used, which makes it difficult to avoid overlap leading to fewer exposures being taken over the allowable time limit (e.g., 0.1 sec.). Embodiments of the present disclosure overcome this limitation by making it possible to use a mixture of sources 110 (or emitters) with sharp and obtuse collimation angles in a manner that temporally overlap, with the sharp angles helping to increase the resolution in the x-y plane, and the obtuse angles helping to increase the image resolution in the z-direction.

Moreover, it may happen in medical or clinical settings that the source(s) 110 and detector 140 are not properly aligned (e.g., the pitch and yaw of the source are non-coplanar with the detector), which may lead to x-ray overlap even at otherwise acceptable SODs. The ability of embodiments of the present disclosure to withstand overlap eliminates this concern, and allows more flexibility in the manner in which patients are x-rayed, e.g., a patient lying in bed, supine may be imaged from the foot of the bed, eliminating the need to suspend a heavy source over the patient.

Embodiments of the present disclosure also have significant advantages over conventional systems with regard to handling different ROIs 165. In cases where the ROI 165 is similar in area to a detector, x-ray overlap allows the edge of the ROI 165 to be well sampled without requiring additional sources 110 or emitters, which in turn increases operation speed. In conventional systems (where x-ray overlap cannot be tolerated), the edge sources or emitters (e.g., the outer rows and columns of emitter on a conventional emitter panel) typically cover a small portion of the ROI. Because emitters, and more specifically x-rays from different emitters, cannot overlap, this requires the operator or radiographer to separately activate the edge emitters, and thus perform more scans than would be necessary under embodiments of the present disclosure.

In cases where the ROI 165 is small compared to a detector, embodiments of the present disclosure may effectively halve acquisition time due to the fact that x-rays from different emitters may overlap effectively covering the entire ROI 165. In this way, an operator or radiographer can take a rapid series of images, and thus mitigate the number of motion artifacts. This feature is especially beneficial in the case of children or frail patients, where movement can be a bigger concern and body thickness is smaller.

Figure 4:
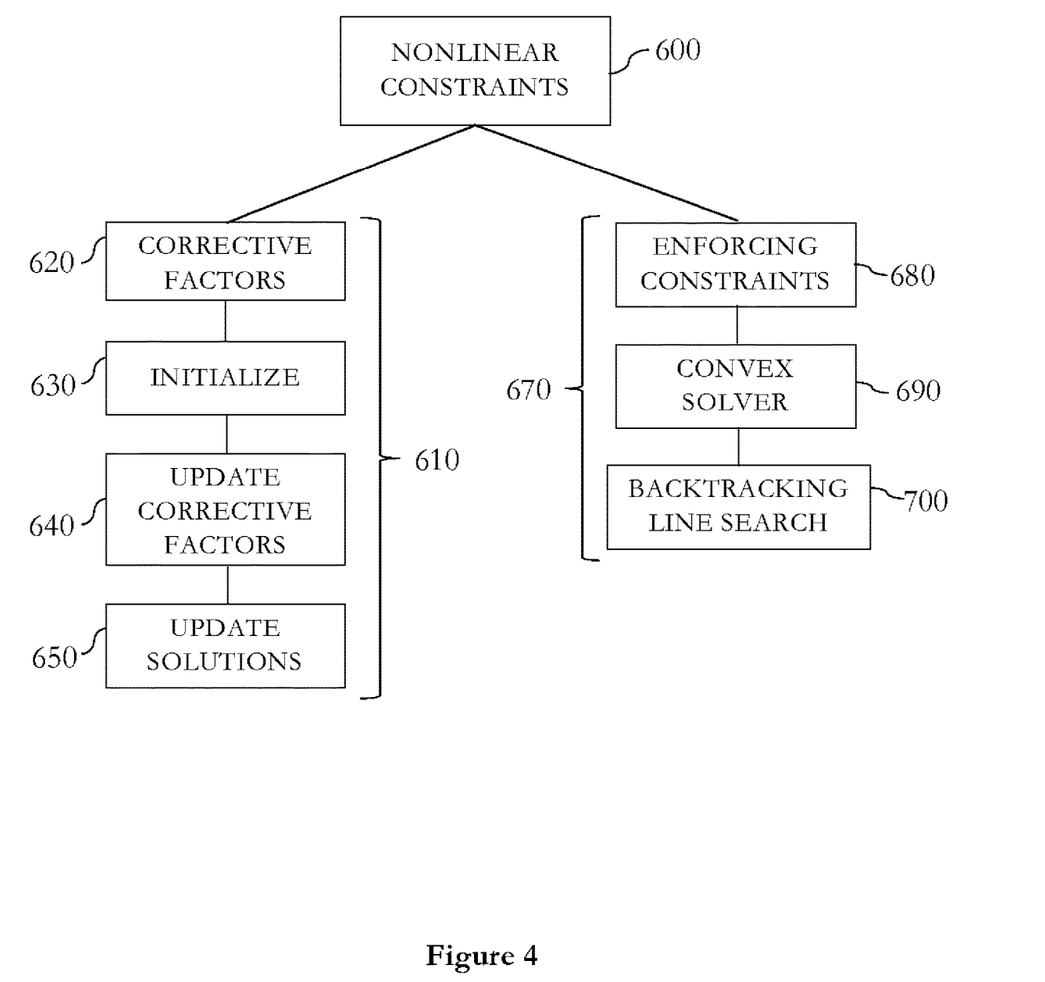
FIG. 4 is a flow chart illustrating an exemplary method of generating an estimate of intensity in accordance with aspects of the present disclosure.

Referring now to FIG. 4, which shows a summary of an exemplary method of generating an estimate of the intensity attributable to each of a plurality of x-ray beams measured at m pixels of a detector using a first algorithm 610 and a second algorithm 670 in accordance with aspects of the present disclosure.

The nonlinear constraints 600 which represent the attenuation of the x-ray beams over the ROI 165 may be satisfied using either one of a first algorithm 610 and second algorithm 670, or a combination thereof.

The first algorithm 610 replaces the nonlinear constraints 600 with corrective factors at step 620. At step 630, the corrective factor values are intialised at the start of the first iteration, before step 640 where they are iteratively updated. At step 650, the first algorithm 610 iteratively updates the intermediate iterative solutions for the estimate of the intensity. The objective function contains a sparsity prior $\|x\|_s$, which is the $L_1$-norm, the Total Variation Norm, or a convex combination of the two.

The second algorithm 670 uses enforcing constraints on the nonlinear constraints at step 680. The second algorithm is then minimized in conjunction with a convex solver at step 690. Finally, the second algorithm 670 uses a backtracking line search at step 700 to solve the estimate of the intensity.

It should be understood that, while embodiments of the present disclosure have been described above, the present invention(s) should not be limited by the foregoing. To the contrary, the foregoing written description, figures, and abstract have been presented for illustrative purposes, and are in no way meant to limit the present invention(s). Indeed, as a person of skill in the art in view of the present disclosure would recognize, various changes can be made to the foregoing without departing from the scope and spirit of the present invention(s).

The invention claimed is:

1. A method of generating an estimate of the intensity attributable to each of a plurality of x-ray beams measured at m pixels of a detector, the method comprising the steps of:
   providing an x-ray detector arranged to generate a signal in response to x-rays incident upon the detector, wherein the signal indicates the intensity of x rays incident upon each of a plurality of pixels of the detector;
   providing a plurality of x-ray sources arranged to emit x-rays such that said x-rays pass through a region of interest (ROI), wherein at least two of the plurality of x-ray sources are arranged to emit x-rays such that said x-rays spatially and temporally overlap at at least one pixel of the detector;
   providing a processing unit arranged to receive the signal indicating the intensity of x-rays incident upon each of the plurality of pixels of the detector and to generate an estimate of the intensity attributable to each of the x-ray beams incident upon the detector;
   generating the estimate using either one of a first algorithm and second algorithm, or combination thereof, to satisfy m nonlinear constraints which represent the attenuation of the x-ray beams over the ROI;
   wherein the first algorithm uses a process of iterative refinement of a corrective factor to linearize the nonlinear constraints; and
   wherein the second algorithm incentivizes the satisfaction of the nonlinear constraints via a penalty term and an enforcing constraint, in conjunction with a convex solver.

2. The method of claim 1, further comprising the step of generating a three-dimensional representation of the ROI using one or more estimates of the intensity attributable to each of the x-ray beams emitted by the plurality of x-ray sources incident upon the detector.

3. The method of claim 1, further comprising the steps of: voxelizing the ROI into a plurality of three-dimensional, non-overlapping voxels and estimating an attenuation coefficient attributable to each said voxel.

4. The method of claim 3, wherein the nonlinear constraint representing the attenuation of the $p_j$ x-ray beams spatially and temporally overlapping at the j-th pixel of the detector is given by $$\psi_j = \sum_{k=1}^{p_j} \frac{I_{E_{jk}}}{\sum_{l=1}^{p_j} I_{E_{jl}}} \exp\left(\sum_{i=1}^{n} -\xi_{ijk} x_i\right),$$

where n is the number of voxels, the measurement $\psi_j$ is given by $$\psi_j := \frac{I_{D_j}}{\sum_{l=1}^{p_j} I_{E_{jl}}},$$

$I_{E_{jk}}$ corresponds to the intensity of radiation emitted at one of the plurality of x-ray sources k in the direction of detector j, $I_{D_j}$ corresponds to the intensity of radiation measured at detector j, $\xi_{ijk}$ denotes the distance travelled by one of the x-rays emanating from the k-th x-ray source through the i-th voxel, and $x_i$ is the attenuation coefficient of the i-th voxel;
   wherein the first algorithm replaces the nonlinear constraint with $$b_j = \tau_j \sum_{i=1}^{n} a_{ij} x_i,$$

where $b_j := \log \psi_j$, $a_{ij} := -\sum_{k=1}^{p_j} \lambda_{jk} \xi_{ijk}$, $\lambda_{jk} := \frac{I_{E_{jk}}}{\sum_{l=1}^{p_j} I_{E_{jl}}}$ and $\tau_j$ is the corrective factor that is adjusted via the process of iterative refinement; and
   wherein the second algorithm uses enforcing constraints that incentivize intermediate iterative solutions $x:=(x_1, \ldots, x_n)$ to satisfy $x \leq \hat{x}$, where $\hat{x}$ is the minimizer, in conjunction with a convex solver.

5. The method of claim 4, wherein the first algorithm iteratively updates each of the corrective factors $\tau_j$ via $$\tau_j \leftarrow \tau_j(x) := \frac{\log\left(\sum_{k=1}^{p_j} \lambda_{jk} \exp\left(\sum_{i=1}^{n} -\xi_{ijk} x_i\right)\right)}{-\sum_{i=1}^{n} \sum_{k=1}^{p_j} \lambda_{jk} \xi_{ijk} x_i}.$$

for j=1, . . . , m after each update of x; and
   wherein the second algorithm incentivizes the satisfaction of the nonlinear constraints corresponding to pixels j=1, . . . , m of the detector via a penalty term, which is $$g(x) = \frac{1}{2\mu} \sum_{j=1}^{m} \left(\sum_{k=1}^{p_j} \lambda_{jk} \exp(r_{jk}^T x) - \psi_j\right)^2,$$

where $\mu > 0$ and $r_{jk} := (-\xi_{1jk}, \ldots, -\xi_{njk})^T$; and
   wherein the second algorithm uses enforcing constraints $$\psi_j := \sum_{k=1}^{p_j} \lambda_{jk} \exp(r_{jk}^T x) \leq \psi_j$$

for pixels j=1, . . . , m to incentivize the intermediate iterative solutions to satisfy $x \leq \hat{x}$, in conjunction with a convex solver.

6. The method of claim 4, wherein the objective function contains a sparsity prior $\|x\|_s$, which is the $L_1$-norm, the Total Variation Norm, or a convex combination of the two.

7. The method of claim 6, wherein the first algorithm iteratively updates x via:

$$x \leftarrow \operatorname*{argmin}_{x \geq 0} \|x\|_s + \frac{1}{2\mu} \|\tau A x - b\|_2^2,$$

where τ is the diagonal matrix with the current values of the corrective factors $\tau_j$ on the diagonal for j=1, ..., m; and wherein the first algorithm updates τ via τ←diag($\tau_1$(x), ..., $\tau_m$(x)) before the next iteration; and wherein the second algorithm is minimised in conjunction with a convex solver to yield $$\min_{x \geq 0} \left\{ \|x\|_1 + \frac{1}{2\mu} \sum_{j=1}^{m} \left( \sum_{k=1}^{p_j} \lambda_{jk} \exp(r_{jk}^T x) - \psi_j \right)^2 \right\},$$

subject to a backtracking line search to enforce the constraints $\psi_j(x) \leq \psi_j$ for all j=1, ..., m at all intermediate solutions x.

8. The method of claim 4, wherein the first algorithm uses $\tau_j$=1 for j=1, ..., m to initialise the values of the corrective factors at the start of the first iteration; and wherein after each update of x via $$x \leftarrow \operatorname*{argmin}_{x \geq 0} \|x\|_s + \frac{1}{2\mu} \|\tau A x - b\|_2^2,$$

the first algorithm subsequently updates τ via:
τ←diag($\tau_1$(x), ..., $\tau_m$(x)); and wherein the second algorithm uses a backtracking line search
λ=1/L
do
λ←λc
$x^{new}$=x−λ∇g(x)
while g($x^{new}$)−g(x)>$\lambda_c$‖∇g(x)‖$^2$ and ∃j s.t. $\psi_j(x^{new})$>$\psi_j$,
where L is a Lipschitz constant for g(x), ∇g(x) is the gradient of g(x), c∈(0,1) is a parameter, and λ is a step length multiplier, followed by an update,
$x^t$=prox$_{\lambda f}$(max{0; $x^{t-1}$−λ∇g($x^{t-1}$)}),
where $x^{t-1}$ denotes the old value of x from the previous iteration t−1 and $x^t$ denotes the updated value of x in the current iteration t, and where $f(x)$ is the sparsity term and prox$_{\lambda f}$ is the prox function associated with λ$f$(x).

9. The method of claim 3, further comprising the process of re-voxelizing the ROI into a plurality of three-dimensional, non-overlapping voxels based on the estimated attenuation coefficients attributable to each of the voxels of the previous voxelization; and further comprising the step of repeating said re-voxelization until a stopping criterion is met.

10. The method of claim 1, further comprising performing a calibration comprising the steps of activating each source to emit x-rays one at a time; and activating sets of sources to emit x-rays such that said x-rays overlap at the pixel of the detector.

11. The method of claim 1, further comprising selecting the two or more sources to emit x-rays so as to optimize at least one of image acquisition speed, image quality, and ROI coverage.

12. An x-ray imaging system arranged to generate an estimate of the intensity attributable to each of a plurality of x-ray beams measured at m pixels of a detector, the system comprising:

an x-ray detector arranged to generate a signal in response to x-rays incident upon the detector, wherein the signal indicates the intensity of x-rays incident upon each of a plurality of pixels of the detector;

a plurality of x-ray sources arranged to emit x-rays such that said x-rays pass through a region of interest (ROI), wherein at least two of the plurality of x-ray sources are arranged to emit x-rays such that said x-rays spatially and temporally overlap at at least one pixel of the detector; and a processing unit arranged to receive the signal indicating the intensity of x-rays incident upon each of the plurality of pixels of the detector and to generate an estimate of the intensity attributable to each of the x-ray beams incident upon the detector, the estimate generated using either one of a first algorithm and second algorithm, or combination thereof, to satisfy m nonlinear constraints which represent the attenuation of the x-ray beams over the ROI;

wherein the first algorithm uses a process of iterative refinement of a corrective factor to linearize the nonlinear constraints; and wherein the second algorithm incentivizes the satisfaction of the nonlinear constraints via a penalty term and an enforcing constraint, in conjunction with a convex solver.

13. The system of claim 12, wherein the processing unit is further arranged to generate a three-dimensional representation of the ROI using one or more estimates of the intensity attributable to each of the two or more x-rays overlapping at the pixel of the detector.

14. The system of claim 13, further comprising a display operably coupled to the processing unit, wherein the display is arranged to display one or more two-dimensional views of the three-dimensional representation of the ROI.

15. The system of claim 12, wherein the plurality of x-ray sources comprises two or more emitter elements of a distributed source array.

16. The system of claim 12, wherein the processing unit is further arranged to voxelize the ROI into a plurality of three-dimensional, non-overlapping voxels; estimate an attenuation coefficient attributable to each said voxel; and re-voxelize the ROI into a plurality of three-dimensional, non-overlapping voxels based on the estimated attenuation coefficients attributable to each said voxel.

17. The system of claim 16, wherein the processing unit is further arranged to repeat said re-voxelization until a stopping criterion is met.

18. The system of claim 12, wherein the plurality of x-ray sources and the detector each include one or more sensors arranged to determine the relative positions of the x-ray sources and the detector.

19. The system of claim 12, further comprising a controller for operating the x-ray imaging system, wherein the controller is arranged to activate a subset of the plurality of x-ray sources.

20. A method of generating an estimate of the intensity attributable to each of a plurality of x-ray beams measured at m pixels of a detector, the method comprising the steps of:

providing an x-ray detector arranged to generate a signal in response to x-rays incident upon the detector, wherein the signal indicates the intensity of x-rays incident upon each of a plurality of pixels of the detector;

providing a plurality of x-ray sources arranged to emit x-rays such that said x-rays pass through a region of interest (ROI), wherein at least two of the plurality of x-ray sources are arranged to emit x-rays such that said x-rays spatially and temporally overlap at at least one pixel of the detector;

providing a processing unit arranged to receive the signal indicating the intensity of x-rays incident upon each of the plurality of pixels of the detector and to generate an estimate of the intensity attributable to each of the x-ray beams incident upon the detector;

generating the estimate using either one of a first algorithm and second algorithm, or combination thereof, to satisfy m nonlinear constraints which represent the attenuation of the x-ray beams over the ROI;

wherein the first algorithm uses a process of iterative refinement of a corrective factor to linearize the nonlinear constraints; and wherein the second algorithm incentivizes the satisfaction of the nonlinear constraints via a penalty term and an enforcing constraint, in conjunction with a convex solver;

generating a three-dimensional representation of the ROI using one or more estimates of the intensity attributable to each of the x-ray beams emitted by the plurality of x-ray sources incident upon the detector;

voxelizing the ROI into a plurality of three-dimensional, non-overlapping voxels and estimating an attenuation coefficient attributable to each said voxel;

wherein the nonlinear constraint representing the attenuation of the $p_j$ x-ray beams spatially and temporally overlapping at the j-th pixel of the detector is given by $$\psi_j = \sum_{k=1}^{p_j} \frac{I_{E_{jk}}}{\sum_{l=1}^{p_j} I_{E_{jl}}} \exp\left(\sum_{i=1}^{n} -\xi_{ijk} x_i\right),$$

where n is the number of voxels, the measurement $\psi_j$ is given by $$\psi_j := \frac{I_{D_j}}{\sum_{l=1}^{p_j} I_{E_{jl}}},$$

$I_{E_{jk}}$ corresponds to the intensity of radiation emitted at one of the plurality of x-ray sources k in the direction of detector j, $I_{D_j}$ corresponds to the intensity of radiation measured at detector j, $\xi_{ijk}$ denotes the distance travelled by one of the x-rays emanating from the k-th x-ray source through the i-th voxel, and $x_i$ is the attenuation coefficient of the i-th voxel;

wherein the first algorithm replaces the nonlinear constraint with $$b_j = \tau_j \sum_{i=1}^{n} a_{ij} x_i,$$

where $b_j := \log\psi_j$, $a_{ij} := -\sum_{k=1}^{p_j} \lambda_{jk} \xi_{ijk}$, $\lambda_{jk} := \frac{I_{E_{jk}}}{\sum_{l=1}^{p_j} I_{E_{jl}}}$ and $\tau_j$ is the corrective factor that is adjusted via the process of iterative refinement; and wherein the second algorithm uses enforcing constraints that incentivize intermediate iterative solutions $x := (x_1, \ldots, x_n)$ to satisfy $x \le \hat{x}$, where $\hat{x}$ is the minimizer, in conjunction with a convex solver;

wherein the first algorithm iteratively updates each of the corrective factors $\tau_j$ via $$\tau_j \leftarrow \tau_j(x) := \frac{\log\left(\sum_{k=1}^{p_j} \lambda_{jk} \exp\left(\sum_{i=1}^{n} -\xi_{ijk} x_i\right)\right)}{-\sum_{i=1}^{n}\sum_{k=1}^{p_j} \lambda_{jk} \xi_{ijk} x_i}.$$

for j=1, . . . , m after each update of x; and wherein the second algorithm incentivizes the satisfaction of the nonlinear constraints corresponding to pixels j=1, . . . , m of the detector via a penalty term, which is $$g(x) = \frac{1}{2\mu} \sum_{j=1}^{m} \left(\sum_{k=1}^{p_j} \lambda_{jk} \exp(r_{jk}^T x) - \psi_j\right)^2,$$

where $\mu > 0$ and $r_{jk} := (-\xi_{1jk}, \ldots, -\xi_{njk})^T$; and wherein the second algorithm uses enforcing constraints $$\psi_j := \sum_{k=1}^{p_j} \lambda_{jk} \exp(r_{jk}^T x) \le \psi_j$$

for pixels j=1, . . . , m to incentivize the intermediate iterative solutions to satisfy $x \le \hat{x}$, in conjunction with a convex solver.

* * * * *